United States Patent
Wu et al.

(10) Patent No.: US 11,678,954 B2
(45) Date of Patent: Jun. 20, 2023

(54) ADJUSTMENT OF TOOTH POSITION IN A VIRTUAL DENTAL MODEL

(71) Applicant: Align Technology, Inc., San Jose, CA (US)

(72) Inventors: Fuming Wu, Pleasanton, CA (US); Vadim Matov, San Jose, CA (US); Artem Borovinskih, San Jose, CA (US); Rene M. Sterental, Palo Alto, CA (US); Pavel Agapov, Palo Alto, CA (US); Anton Spiridonov, Cary, NC (US); Anatoliy Boltunov, Moscow (RU)

(73) Assignee: Align Technology, Inc., San Jose, CA (US)

( * ) Notice: Subject to any disclaimer, the term of this patent is extended or adjusted under 35 U.S.C. 154(b) by 556 days.

(21) Appl. No.: 16/841,556

(22) Filed: Apr. 6, 2020

(65) Prior Publication Data
US 2020/0229902 A1    Jul. 23, 2020

Related U.S. Application Data

(60) Continuation of application No. 15/227,401, filed on Aug. 3, 2016, now Pat. No. 10,610,332, which is a division of application No. 13/477,879, filed on May 22, 2012, now Pat. No. 9,414,897.

(51) Int. Cl.
| | |
|---|---|
| *A61C 7/00* | (2006.01) |
| *G06T 19/20* | (2011.01) |
| *G06F 30/00* | (2020.01) |
| *G16H 20/00* | (2018.01) |
| *G16H 20/40* | (2018.01) |

(52) U.S. Cl.
CPC .............. *A61C 7/002* (2013.01); *G06F 30/00* (2020.01); *G06T 19/20* (2013.01); *A61C 2007/004* (2013.01); *G06T 2210/41* (2013.01); *G16H 20/00* (2018.01); *G16H 20/40* (2018.01)

(58) Field of Classification Search
CPC .......... A61C 7/002; G06F 30/00; G06T 19/20
See application file for complete search history.

(56) References Cited

U.S. PATENT DOCUMENTS

| | | | |
|---|---|---|---|
| 5,975,893 | A | 11/1999 | Chishti et al. |
| 6,227,850 | B1 | 5/2001 | Chishti et al. |
| 6,227,851 | B1 | 5/2001 | Chishti et al. |
| 6,299,440 | B1 | 10/2001 | Phan et al. |
| 6,318,994 | B1 | 11/2001 | Chishti et al. |
| 6,371,761 | B1 | 4/2002 | Cheang et al. |
| 6,386,878 | B1 | 5/2002 | Pavlovskaia et al. |
| 6,406,292 | B1 | 6/2002 | Chishti et al. |
| 6,409,504 | B1 | 6/2002 | Jones et al. |
| 6,457,972 | B1 | 10/2002 | Chishti et al. |
| 6,488,499 | B1 | 12/2002 | Miller |
| 6,514,074 | B1 | 2/2003 | Chishti et al. |
| 6,554,611 | B2 | 4/2003 | Chishti et al. |
| 6,582,229 | B1 | 6/2003 | Miller et al. |
| 6,602,070 | B2 | 8/2003 | Miller et al. |
| 6,621,491 | B1 | 9/2003 | Baumrind et al. |
| 6,688,886 | B2 | 2/2004 | Hughes et al. |
| 6,726,478 | B1 | 4/2004 | Isiderio et al. |
| 6,729,876 | B2 | 5/2004 | Chishti et al. |
| 6,739,869 | B1 | 5/2004 | Taub et al. |
| 6,767,208 | B2 | 7/2004 | Kaza |
| 6,783,360 | B2 | 8/2004 | Chishti |
| 7,040,896 | B2 | 5/2006 | Pavlovskaia et al. |
| 7,063,532 | B1 | 6/2006 | Jones et al. |
| 7,074,038 | B1 | 7/2006 | Miller |
| 7,074,039 | B2 | 7/2006 | Kopelman et al. |
| 7,077,647 | B2 | 7/2006 | Choi et al. |
| 7,108,508 | B2 | 9/2006 | Hedge et al. |
| 7,134,874 | B2 | 11/2006 | Chishti et al. |
| 7,156,661 | B2 | 1/2007 | Choi et al. |
| 7,160,107 | B2 | 1/2007 | Kopelman et al. |
| 7,241,142 | B2 | 7/2007 | Abolfathi et al. |
| 7,293,988 | B2 | 11/2007 | Wen |
| 7,309,230 | B2 | 12/2007 | Wen |
| 7,357,634 | B2 | 4/2008 | Knopp |
| 7,555,403 | B2 | 6/2009 | Kopelman et al. |
| 7,637,740 | B2 | 12/2009 | Knopp |
| 7,689,398 | B2 | 3/2010 | Cheng et al. |
| 7,736,147 | B2 | 6/2010 | Kaza et al. |
| 7,746,339 | B2 | 6/2010 | Matov et al. |
| 7,844,356 | B2 | 11/2010 | Matov et al. |
| 7,844,429 | B2 | 11/2010 | Matov et al. |
| 7,865,259 | B2 | 1/2011 | Kuo et al. |

(Continued)

*Primary Examiner* — Jerry Lin
(74) *Attorney, Agent, or Firm* — Shay Glenn LLP

(57) ABSTRACT

The present disclosure provides computing device implemented methods, computing device readable media, and systems for adjustment of tooth position in a virtual dental model. Virtual dental modeling can include detecting space and/or collision between posterior teeth of an upper jaw and posterior teeth of a lower jaw in a virtual dental model that has been set in a preliminary target position. An energy function can be defined including the space and/or collision, tooth root movement, and align points. Weights can be assigned for each variable in the energy function. A position of the posterior teeth of the upper jaw and the posterior teeth of the lower jaw can be adjusted in six degrees of freedom to minimize the energy function. The detection, definition, assignment, and adjustment can be repeated until the energy function converges. The weights can be adjusted to reduce the space and/or collision.

21 Claims, 11 Drawing Sheets

(56) References Cited

U.S. PATENT DOCUMENTS

| | | |
|---|---|---|
| 7,878,804 B2 | 2/2011 | Korytov et al. |
| 7,880,751 B2 | 2/2011 | Kuo et al. |
| 7,904,308 B2 | 3/2011 | Arnone et al. |
| 7,930,189 B2 | 4/2011 | Kuo |
| 7,942,672 B2 | 5/2011 | Kuo |
| 7,970,627 B2 | 6/2011 | Kuo et al. |
| 7,970,628 B2 | 6/2011 | Kuo et al. |
| 8,038,444 B2 | 10/2011 | Kitching et al. |
| 8,044,954 B2 | 10/2011 | Kitching et al. |
| 8,075,306 B2 | 12/2011 | Kitching et al. |
| 8,092,215 B2 | 1/2012 | Stone-Collonge et al. |
| 8,099,268 B2 | 1/2012 | Kitching et al. |
| 8,108,189 B2 | 1/2012 | Chelnokov et al. |
| 8,126,726 B2 | 2/2012 | Matov et al. |
| 8,260,591 B2 | 9/2012 | Kass et al. |
| 8,275,180 B2 | 9/2012 | Kuo |
| 8,401,826 B2 | 3/2013 | Cheng et al. |
| 8,439,672 B2 | 5/2013 | Matov et al. |
| 8,562,338 B2 | 10/2013 | Kitching et al. |
| 8,591,225 B2 | 11/2013 | Wu et al. |
| 8,788,285 B2 | 7/2014 | Kuo |
| 8,843,381 B2 | 9/2014 | Kuo et al. |
| 8,874,452 B2 | 10/2014 | Kuo |
| 8,896,592 B2 | 11/2014 | Boltunov et al. |
| 8,930,219 B2 | 1/2015 | Trosien et al. |
| 9,037,439 B2 | 5/2015 | Kuo et al. |
| 9,060,829 B2 | 6/2015 | Sterental et al. |
| 9,125,709 B2 | 9/2015 | Matty |
| 9,211,166 B2 | 12/2015 | Kuo et al. |
| 9,220,580 B2 | 12/2015 | Borovinskih et al. |
| 9,364,296 B2 | 6/2016 | Kuo |
| 9,375,300 B2 | 6/2016 | Matov et al. |
| 9,492,245 B2 | 11/2016 | Sherwood et al. |
| 9,642,678 B2 | 5/2017 | Kuo |
| 10,248,883 B2 | 4/2019 | Borovinskih et al. |
| 10,342,638 B2 | 7/2019 | Kitching et al. |
| 10,463,452 B2 | 11/2019 | Matov et al. |
| 10,595,966 B2 | 3/2020 | Carrier, Jr. et al. |
| 10,617,489 B2 | 4/2020 | Grove et al. |
| 10,722,328 B2 | 7/2020 | Velazquez et al. |
| 10,758,322 B2 | 9/2020 | Pokotilov et al. |
| 10,779,718 B2 | 9/2020 | Meyer et al. |
| 10,792,127 B2 | 10/2020 | Kopelman et al. |
| 10,828,130 B2 | 11/2020 | Pokotilov et al. |
| 10,835,349 B2 | 11/2020 | Cramer et al. |
| 10,973,611 B2 | 4/2021 | Pokotilov et al. |
| 10,996,813 B2 | 5/2021 | Makarenkova et al. |
| 10,997,727 B2 | 5/2021 | Xue et al. |
| 2003/0008259 A1 | 1/2003 | Kuo et al. |
| 2003/0143509 A1 | 7/2003 | Kopelman et al. |
| 2003/0207227 A1 | 11/2003 | Abolfathi |
| 2004/0137400 A1 | 7/2004 | Chishti et al. |
| 2004/0152036 A1 | 8/2004 | Abolfathi |
| 2004/0197728 A1 | 10/2004 | Abolfathi et al. |
| 2004/0259049 A1 | 12/2004 | Kopelman et al. |
| 2005/0182654 A1 | 8/2005 | Abolfathi et al. |
| 2005/0244791 A1 | 11/2005 | Davis et al. |
| 2006/0127836 A1 | 6/2006 | Wen |
| 2006/0127852 A1 | 6/2006 | Wen |
| 2006/0127854 A1 | 6/2006 | Wen |
| 2006/0275731 A1 | 12/2006 | Wen et al. |
| 2006/0275736 A1 | 12/2006 | Wen et al. |
| 2008/0306724 A1 | 12/2008 | Kitching et al. |
| 2010/0009308 A1 | 1/2010 | Wen et al. |
| 2010/0068672 A1 | 3/2010 | Arjomand et al. |
| 2010/0068676 A1 | 3/2010 | Mason et al. |
| 2010/0092907 A1 | 4/2010 | Knopp |
| 2010/0167243 A1 | 7/2010 | Spiridonov et al. |
| 2010/0280798 A1* | 11/2010 | Pattijn .................. A61C 7/12 703/1 |
| 2013/0204599 A1 | 8/2013 | Matov et al. |
| 2016/0135925 A1 | 5/2016 | Mason et al. |
| 2016/0242870 A1 | 8/2016 | Matov et al. |
| 2016/0310235 A1 | 10/2016 | Derakhshan et al. |
| 2017/0273760 A1 | 9/2017 | Morton et al. |
| 2018/0168775 A1 | 6/2018 | Derakhshan et al. |
| 2018/0280118 A1 | 10/2018 | Cramer |
| 2019/0029784 A1 | 1/2019 | Moalem et al. |
| 2019/0053876 A1 | 2/2019 | Sterental et al. |
| 2019/0076214 A1 | 3/2019 | Nyukhtikov et al. |
| 2019/0105127 A1 | 4/2019 | Velazquez et al. |
| 2019/0175303 A1 | 6/2019 | Akopov et al. |
| 2019/0192259 A1 | 6/2019 | Kopelman et al. |
| 2019/0328487 A1 | 10/2019 | Levin et al. |
| 2019/0328488 A1 | 10/2019 | Levin et al. |
| 2019/0333622 A1 | 10/2019 | Levin et al. |
| 2019/0343601 A1 | 11/2019 | Roschin et al. |
| 2019/0350680 A1 | 11/2019 | Chekh et al. |
| 2019/0357997 A1 | 11/2019 | Shi et al. |
| 2020/0000551 A1 | 1/2020 | Li et al. |
| 2020/0000552 A1 | 1/2020 | Mednikov et al. |
| 2020/0000554 A1 | 1/2020 | Makarenkova et al. |
| 2020/0000555 A1 | 1/2020 | Yuryev et al. |
| 2020/0085546 A1 | 3/2020 | Li et al. |
| 2020/0105028 A1 | 4/2020 | Gao et al. |
| 2020/0107915 A1 | 4/2020 | Roschin et al. |
| 2020/0155274 A1 | 5/2020 | Pimenov et al. |
| 2020/0214800 A1 | 7/2020 | Matov et al. |
| 2020/0297458 A1 | 9/2020 | Roschin et al. |
| 2020/0306011 A1 | 10/2020 | Chekhonin et al. |
| 2020/0306012 A1 | 10/2020 | Roschin et al. |
| 2020/0315744 A1 | 10/2020 | Cramer |
| 2020/0360109 A1 | 11/2020 | Gao et al. |
| 2021/0073998 A1 | 3/2021 | Brown et al. |

* cited by examiner

ADJUSTMENT OF TOOTH POSITION IN A VIRTUAL DENTAL MODEL

CROSS REFERENCE TO RELATED APPLICATIONS

This application is a continuation of U.S. application Ser. No. 15/227,401, filed Aug. 3, 2016, which is a divisional of U.S. application Ser. No. 13/477,879, filed May 22, 2012, each of which is herein incorporated by reference in its entirety.

INCORPORATION BY REFERENCE

All publications and patent applications mentioned in this specification are incorporated herein by reference in their entirety to the same extent as if each individual publication or patent application was specifically and individually indicated to be incorporated by reference.

BACKGROUND

The present disclosure is related generally to the field of dental treatment. More particularly, the present disclosure is related to methods, devices, and systems for adjustment of tooth position in a virtual dental model.

Dental treatments may involve repositioning misaligned teeth and changing bite configurations for improved cosmetic appearance and dental function. Orthodontic repositioning can be accomplished, for example, by applying controlled forces to one or more teeth over a period of time.

As an example, orthodontic repositioning may be provided through a dental process that uses positioning appliances for realigning teeth. Such appliances may utilize a thin shell of material having resilient properties, referred to as an "aligner," that generally conforms to a patient's teeth but is slightly out of alignment with a current tooth configuration.

Placement of such an appliance over the teeth may provide controlled forces in specific locations to gradually move the teeth into a new configuration. Repetition of this process with successive appliances in progressive configurations can move the teeth through a series of intermediate arrangements to a final desired arrangement.

Such systems typically utilize materials that are light weight and/or transparent to provide as a set of appliances that can be used serially such that as the teeth move, a new appliance can be implemented to further move the teeth.

With computing device-aided teeth treatment systems, an initial digital data set (IDDS) representing an initial tooth arrangement may be obtained. The IDDS may be obtained in a variety of ways.

For example, the patient's teeth may be imaged to obtain digital data using direct and/or indirect structured light, X-rays, three-dimensional X-rays, lasers, destructive scanning, computing device-aided tomographic images or data sets, magnetic resonance images, intra-oral scanning technology, photographic reconstruction, and/or other imaging techniques. The IDDS can include an entire mouth tooth arrangement, some, but not all teeth in the mouth, and/or it can include a single tooth.

A positive model and/or negative impression of the patient's teeth or a tooth may be scanned using an X-ray, laser scanner, destructive scanner, structured light, and/or other range acquisition system to produce the IDDS. The data set produced by the range acquisition system may be converted to other formats to be compatible with the software which is used for manipulating images within the data set, as described herein.

After scanning, a virtual dental model including teeth of an upper jaw and a lower jaw may be generated. However, the upper jaw and lower jaws of the virtual dental model may not be aligned with respect to each other. Thus, a bite setting operation may be performed to align the virtual dental model including the upper and lower jaws. Other operations may be performed to reposition the teeth within the virtual dental model to a desired final position representing a desired final position for the physical teeth of the patient.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
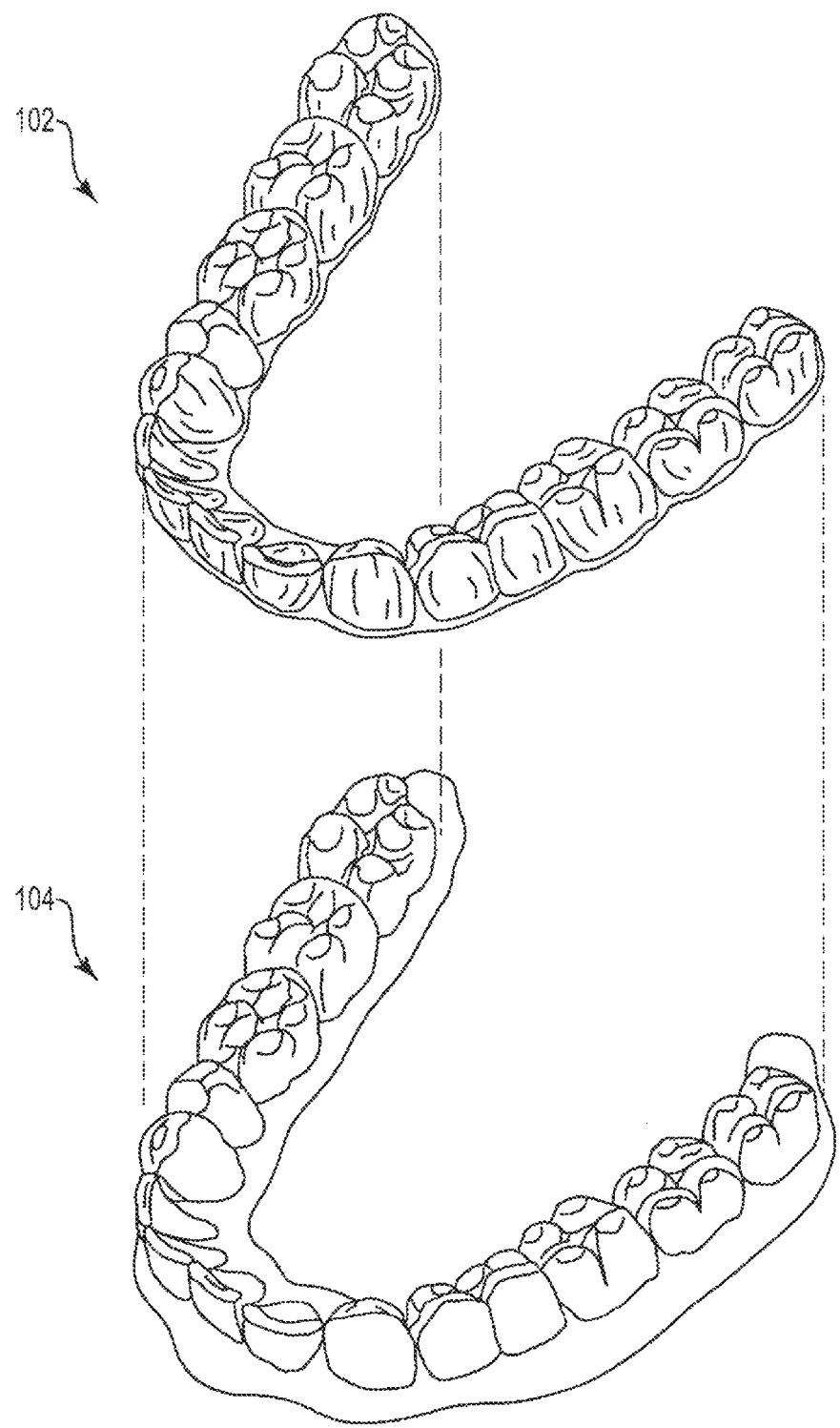
FIG. 1 illustrates a dental position adjustment appliance being applied to a set of teeth according to one or more embodiments of the present disclosure.

Setting up a final position of teeth in a virtual dental model includes a number of steps, some of which have previously included the use of human input (e.g., through the use of a computing device) to improve a quality of the final position that may be generated by a computing device. For example, one previous approach included constructing a desired archform for the virtual dental model, snapping the teeth of the virtual dental model to the desired archform, and then manually adjusting the teeth to improve occlusion between the upper and lower jaws of the virtual dental model. Manual adjustment may introduce errors and/or inefficiencies into the process that could be remediated by an automatic (e.g., fully automatic) final position setup. However, there is no straightforward mechanism to automate the manual adjustment process that may be based on human intuition or user preference rather than a formulaic approach.

Setting up a final position can include resolving a number of considerations for the final position such as teeth alignment within an arch, occlusion of anterior and posterior teeth, correcting overbite and/or overjet, etc. A number of embodiments of the present disclosure can provide an automatic final position setup with minimal manual adjustment for a virtual dental model. Minimal manual adjustment can include simple manual adjustment functions to fine tune an "ideal" result for the final position setup rather than manual inputs of a number of features, such as archform adjustment, symmetry occlusal archform, local tooth position, inter-proximal reduction (IPR), anterior and posterior occlusion, biting simulation, among other features. One or more embodiments of the present disclosure can include automatic IPR design, fast crowding computation, fast collision depth detection, anterior and/or posterior occlusion measurement, and/or biting simulation, among other features.

In general, a goal of orthodontic treatment can be to correct malocclusions such as crooked teeth, spacing (e.g., gaps between teeth), crowding (e.g., overlapping teeth), deep-bite (e.g., upper anterior teeth being too low), open bite (e.g., a gap between upper and lower jaws in the anterior section), and/or cross bite (e.g., an upper tooth behind a lower tooth), among others.

The present disclosure provides computing device implemented methods, computing device readable media, and systems for adjustment of tooth position in a virtual dental model. Virtual dental modeling can include detecting space and/or collision between a number of posterior teeth of an upper jaw and a number of posterior teeth of a lower jaw in a virtual dental model that has been set in a preliminary target position. An energy function can be defined including the space and/or collision, tooth root movement, and align points. Weights can be assigned for each variable in the energy function. A position of the number of posterior teeth of the upper jaw and the number of posterior teeth of the lower jaw can be adjusted in six degrees of freedom to minimize the energy function. The detection, definition, assignment, and adjustment can be repeated until the energy function converges. The weights can be adjusted to reduce the space and/or collision.

Feature points, such as cusps and grooves, can be automatically calculated for teeth (e.g., posterior teeth) of jaws in a virtual dental model. For example, a cusp point can be a subset of local maximum extremes of points in the data comprising a particular tooth and groove points can be calculated as a subset of local minimum extremes of the data comprising the particular tooth. Between an upper and lower jaw, for good occlusion, the cusps and grooves should correspond to each other as described in more detail below.

Based on the feature points, for each jaw in the virtual dental model, feature splines can be calculated (e.g., labial cusp feature splines, lingual cusp feature splines, groove features splines, etc.). The feature splines calculated based on a current position of the teeth in the virtual dental model can be referred to as current feature splines, while feature splines calculated based on a target dentition can be referred to as target feature splines. The target feature splines can be calculated based on interaction between respective feature splines of both jaws (e.g., where the lingual cusps feature spline of the upper jaw corresponds to the groove feature spline of the lower jaw).

An attractive force can be modeled between a feature point on one of the number of current feature splines and a corresponding feature point on a corresponding one of the number of target feature splines. The corresponding feature point on the target feature spline can be the feature point from the current feature spline projected to the target feature spline. The modeled attractive force can encourage the feature point to move from its current position to its target position.

A repulsive (e.g., collision) force can be modeled for collisions between a point in upper jaw and a point in the lower jaw. A collision in the virtual dental model can be represented as a set of collision spots, where each spot is connected to a component of intersection between shapes of two different teeth. A mass center, normal, and depth can be calculated for each collision spot. The repulsive force can be implemented for pairs of collision points such that a particular collision spot is pushed along a normal where the tooth movement is equal to half of the depth, for example.

A stabilization force can be modeled to limit motion of a tooth to be within a range of motion within one of the upper jaw and the lower jaw. Stabilization forces can be implemented as pairs of points for matching, however the points are matched to themselves (e.g., to discourage tooth movement in the virtual dental model). For example, a tooth root can be used as a stabilization point. In some embodiments, anisotropic matching constraints can be applied to the pairs of points (e.g., penalties during matching that are differently controlled for tooth rotation and translation degrees of freedom). Using anisotropic penalties for rotation can allow for selective control and suppress undesired tooth rotation such as angulation and/or angular rotation. Using anisotropic penalties for translation can allow for selective control and suppress undesired tooth translation such as mesial/distal shifts and/or extrusion/intrusion.

Combining the attractive forces, repulsive forces, and stabilization forces in the virtual dental model can allow for incremental construction of a target position during an iterative process with relatively few steps. However, some embodiments may exclude the use of collision forces in the calculation of the target position and may resolve possible inter-jaw tooth collisions from the current position without using the attractive forces.

On each step, for example, the forces can be recalculated. The forces can be weighted, and the weights can be adjusted so that tooth movement within a particular step (e.g., defined treatment step as described herein) is within a specified tolerance (e.g., for patient comfort, etc.). The sequence of such steps can provide the tooth movement trajectory from the current position to the target position as part of a treatment plan. Additional details of biting simulation and force modeling are described below with respect to FIG. 8.

FIG. 1 illustrates a dental position adjustment appliance being applied to a set of teeth according to one or more embodiments of the present disclosure. Appliances according to the present disclosure can include, in some embodiments, a plurality of incremental dental position adjustment appliances. The appliances, such as appliance 102 illustrated in FIG. 1, can be utilized to affect incremental repositioning of individual teeth in the jaw, among other suitable uses. Appliances, such as appliance 102, can be fabricated according to a virtual dental model that has had positions of a number of teeth adjusted according to one or more embodiments of the present disclosure.

Appliances can include any positioners, retainers, and/or other removable appliances for finishing and maintaining teeth positioning in connection with a dental treatment. These appliances may be utilized by the treatment professional in performing a treatment plan. For example, a treatment plan can include the use of a set of appliances, created according to models described herein.

An appliance (e.g., appliance 102 in FIG. 1) can, for example, be fabricated from a polymeric shell, and/or formed from other material, having a cavity shaped to receive and apply force to reposition one or more teeth from one teeth arrangement to a successive teeth arrangement. The shell may be designed to fit over a number of, or in many instances all, teeth 104 present in the upper and/or lower jaw.

Figure 2:
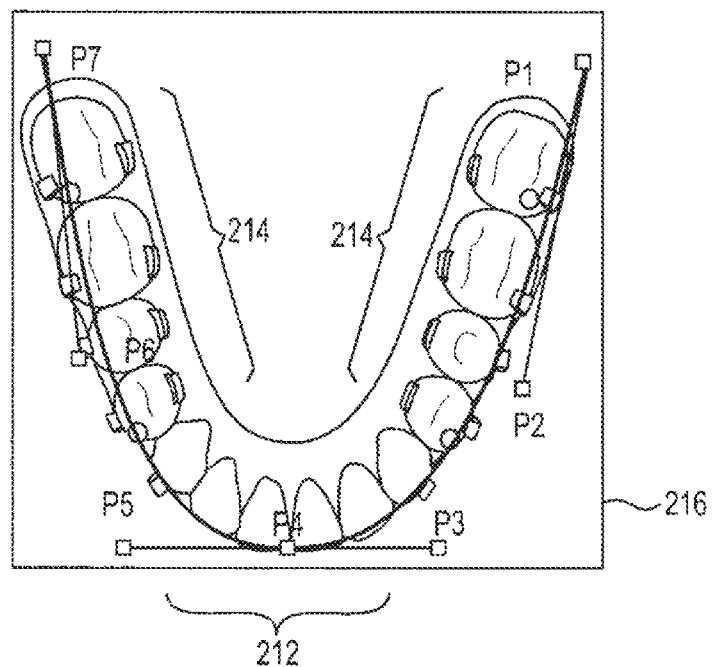
FIG. 2 illustrates a virtual archform according to one or more embodiments of the present disclosure.

FIG. 2 illustrates a virtual archform 216 according to one or more embodiments of the present disclosure. In general, an archform 216 can be a smooth curve that passes through feature points in the teeth in a dental arch. The archform 216 can serve as a baseline for alignment of the teeth. One dental arch can have multiple archforms based on the feature points used to determine the archform (e.g., a contact point archform, a facial axis archform, an occlusal archform, etc.). For example, an occlusal archform can pass through occlusion points of the upper and lower jaws, where for the lower jaw, the archform passes through the buccal ridges of posterior teeth 214 and incisal ridges of anterior teeth 212, and where for the upper jaw, the archform can pass through the central groove of molar and premolar and the contact points of the anterior teeth 212. For a desired final position setup, the occlusal archforms for the upper and lower jaw can match with each other such that teeth in the virtual dental model can move freely along the occlusal archform to solve space and/or crowding problems while maintaining anterior and posterior occlusion.

In general, the archform 216 can be a smooth three-dimensional (3D) curve such that it can control both horizontal and vertical tooth movement. The archform 216 can have anterior symmetry such that the anterior teeth 212 are symmetric on opposite sides of the jaw. The archform 216 can be adjustable in size and shape. The example illustrated in FIG. 2 includes a number of control points (e.g., $P_1$, $P_2$, $P_3$, $P_4$, $P_5$, $P_6$, and $P_7$) to control the shape and position of the archform 216.

In some embodiments, the archform 216 can be formed from a number of segments of a cubic spline curve. Examples of such splines include a labial cusps feature spline (e.g., a spline formed based on cusps on the labial side of the teeth), a lingual cusps feature spline (e.g., a spline formed based on cusps on the lingual side of the teeth), and a grooves feature spline (e.g., a spline formed based on the grooves in the teeth), among others.

An occlusal archform can be created from occlusal points in a jaw. An occlusal point can be detected for each tooth based on tooth type. For a lower incisor, the occlusal point can be detected by finding a facial plane that best fits the buccal vertices of the incisor, detecting the ridge vertices that are highest points in a direction from root-to-ridge of the incisor for different directions along the ridge, project ridge vertices into the facial plane, use a line to best fit the projected ridge vertices (e.g., the ridge line of the tooth), detect the tip point (e.g., the highest vertex near the facial axis point), and project the top point to the ridge line as the occlusal point.

For upper central incisors, the occlusal point can be detected and shifted in the buccal direction for a first distance (e.g., 1.0 mm) and in a direction from ridge-to-root for a second distance (e.g., 2.5 mm). The first and second distances can be determined according to a desired overbite and overjet distance. For an upper lateral incisor, the occlusal point can be shifted a third distance (e.g., 2.0 mm) in a direction from ridge-to-root. Selecting a third distance less than the second distance can make lateral incisor leveling higher than the central incisors.

For a lower premolar and/or canine, the occlusal point can be detected by constructing a middle plane, which can be a plane extending in a direction from root-to-tip and from facial-to-lingual portions of the tooth, finding a vertex that's near the middle plane and in the buccal side of the tooth, then projecting the vertex into the middle plane as a facial middle vertex, using a line to best fit all facial middle vertices, and projecting the tip point into the facial middle line to get the occlusal point.

For an upper canine, the occlusal point can be shifted a first distance (e.g., 1.5 mm) in a facial-lingual direction and a second distance (e.g., 3.0 mm) in a tip-root direction. When the second distance from the upper canine is greater than the second distance for the central incisor, the tip of the upper incisor can be lower than the central incisor.

For an upper premolar and molar, the occlusal point can be the center of the crown surface. For example, the center of the crown surface can be the point where a central axis, in a root-tip direction, passes through the tooth crown occlusal surface.

An occlusal plane for each jaw in the virtual dental model can be created. A normal of an occlusal plane can be defined as a Z-direction of an arch coordinate system. Crown centers can be projected into the occlusal plane. Middle points of paired crown centers (e.g., crown centers of left and right second molars) can be computed. A line that is best fit to the middle points can be defined as the Y-axis. The X-axis can be defined as the line that passes the crown center of the second molars.

A first initial archform (e.g., an initial lower archform) can be constructed from initial teeth positions by best fitting the archform to feature points. A second initial archform (e.g., an initial upper archform) can be constructed based on the first initial archform (e.g., by enlarging the anterior, such as by moving the control points $P_1$ and $P_7$ to make the archform wider and/or by adding extended occlusal points to extend the archform posterior in the direction of the posterior occlusal points and enable teeth distalization in the archform).

To help keep the archform smooth and the anterior teeth symmetric, the following constraints can be applied to the control points: $P_4.x=0$, $P_3.x=-P_5.x$ (to make the anterior symmetric to the middle of the arch); $P_3.y=P_4.y=P_5.y$ (to keep the anterior perpendicular to the middle of the arch); and $P_3.z=P_4.z=P_5.z$ (to keep the anterior flat). Then, the three anterior control points $P_3$, $P_4$, and $P_5$, are $P_3=(-w,l,h)$, $P_4=(0,l,h)$, $P_5=(w,l,h)$, where "w" is the anterior width, "l" is the arch length, and "h" is the anterior height. Therefore, the seven control points can be reduced to five control points ($P_1$, $P_2$, $P_6$, $P_7$, Q), where Q=(w,l,h).

Points used to estimate the archform are referred to herein as $Q_1, Q_2, \ldots, Q_n$, where $Q_1$ and $Q_n$ are extended occlusal points and the others are occlusal points. A spline curve can be best fit by computing the distance of one point to a next point as $l_i$, i=1, 2, ... (n−1) and the length of two segments as $$l_a = \sum_{i=1}^{m-2} l_i + \frac{l_{m-1}}{2}, \ l_b = \sum_{i=m}^{n-1} l_i + \frac{l_{m-1}}{2},$$

where m−1 and m are the two center points in the curve. The parameter of the point $Q_i$ can be computed as $$u_i = u_{i-1} + \frac{l_i}{l_a},$$

if $Q_i$ is in the first segment and $$u_i = u_{i-1} + \frac{l_i}{l_b},$$

if $Q_i$ is in the second segment. The least square function $$J = \sum_{i=1}^{n} \|P(u_i) - Q_i\|^2$$

can be solved, where $P(u_i)$ is a point in the spline curve with control points $P_1$, $P_2$, $P_6$, $P_7$, Q and parameter $u_i$, as:

$$t = u$$

$$P = (1-t)^3 P_1 + 3*t(1-t)^2 P_2 + 3*t^2(1-t)P_3 + t^3 P_4$$

if it is in the first section, and as:

$$t = u - 1$$

$$P = (1-t)^3 P_4 + 3*t(1-t)^2 P_5 + 3*t^2(1-t)P_6 + t^3 P_7$$

if it is in the second section, where P3, P4, P5 is the linear function of Q.

The upper archform can be constructed from the lower archform. The posterior of the upper archform can be set equal to the posterior of the lower archform. The anterior difference can be defined as $w_d$, $l_d$, $h_d$ in the X,Y,Z direction. The upper control points can be defined as:

$$P_2{}^u = P_2{}^l + [0.8*w_d, 0, -1.2*h_d]^T$$

$$P_3{}^u = P_3{}^l + [-w_d, l_d, h_d]^T$$

$$P_4{}^u = P_4{}^l + [0, l_d, h_d]^T$$

$$P_5{}^u = P_5{}^l + [w_d, l_d, h_d]^T$$

$$P_6{}^u = P_6{}^l + [-0.8*w_d, 0, -1.2*h_d]^T$$

The anterior difference values $w_d$, $l_d$, $h_d$ can be adjusted to change the anterior occlusion (e.g., overjet, overbite).

Some examples of orthodontic arch adjustments include anterior expansion/contraction, arch shape change (e.g., from a "U" shape to a "V" shape), leveling of the anterior (e.g., changing the Spee curve), and/or posterior expansion (e.g., left and/or right), among others.

As an example, a desired change of an archform can include anterior expansion E, anterior left movement $M_l$, anterior right movement $M_r$, and anterior leveling L. The control points can be changed as:

$$P_2 \mathrel{+}= \begin{bmatrix} 0.6*M_l \\ 0 \\ -1.2*L \end{bmatrix}$$

$$P_3 \mathrel{+}= \begin{bmatrix} -0.4E - 1.0*M_l \\ 0.6*E \\ 1.0*L \end{bmatrix}$$

$$P_4 \mathrel{+}= \begin{bmatrix} 0.0 \\ 0.6*E \\ 1.0*L \end{bmatrix}$$

$$P_5 \mathrel{+}= \begin{bmatrix} 0.4*E + 1.0*M_r \\ 0.6*E \\ 1.0*L \end{bmatrix}$$

$$P_6 \mathrel{+}= \begin{bmatrix} 0.6*M_r \\ 0 \\ -1.2*L \end{bmatrix}$$

Figure 3:
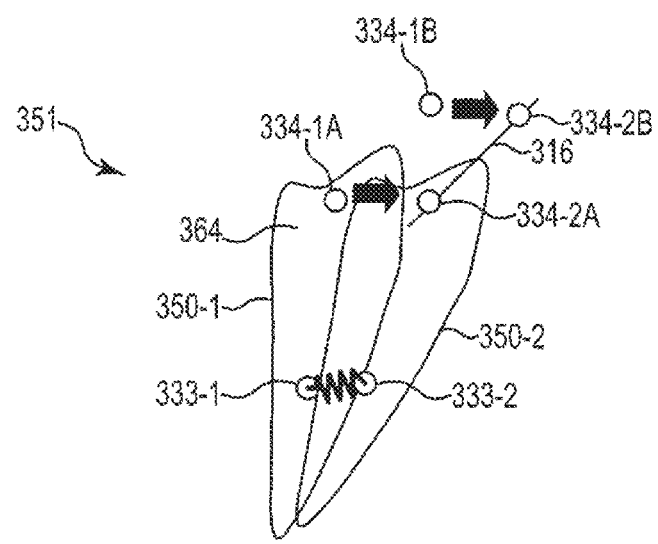
FIG. 3 illustrates a virtual dental model of a tooth with a number of align points and an archform according to one or more embodiments of the present disclosure.

FIG. 3 illustrates a virtual dental model 351 of a tooth 364 with a number of align points 334-1A, 334-1B, 334-2A, 334-2B and an archform 316 according to one or more embodiments of the present disclosure. The virtual dental model 351 includes the tooth 364 in a first position 350-1 with align points 334-1A and 334-1B and in a second position 350-2 with corresponding align points 334-2A and 334-2B. The align points are generally referred to as align points 334.

Because the tooth 364 is a 3D object, alignment of only the occlusal point, as described herein, cannot guarantee alignment of the tooth 364 as a whole. As such, two align points 334 can be used for each tooth 364 to align to the archform 316 and a third point (e.g., a root center) can be used to define the transformation for the tooth 364. The tooth 364 in the first position 350-1 includes root center 333-1 and the tooth 364 in the second position 350-2 includes corresponding root center 333-2. The root center is generally referred to as root center 333.

For example, two align points 334 can be created for the tooth 364 (e.g., one on the mesial side of the occlusal point and one on the distal side of the occlusal point). As described herein, the align points 334 can be based on the occlusal point and the facial axis basis of the tooth 364. The facial axis basis can be defined as the basis (e.g., coordinate system) near the facial axis point using the facial axis point as the origin. The X-axis can be defined as the normal direction near the facial axis point. The Z-axis can be defined as the facial axis of clinical crown (FACC) direction. The align points can be defined within a particular distance (e.g., 2 mm) of the occlusal point in a direction along the Y-axis, perpendicular to the FACC line.

Align points 334-1A and 334-1B for the tooth 364 can be moved to the archform 316. Two align points 334-2A and 334-2B in the archform 316 are based on the archform basis. For any point in the archform 316, the origin of the archform basis is the point itself. The Z-axis can be defined as the occlusal plane norm. The X-axis can be perpendicular to the Z-axis and to a tangent of the archform 316. The align points 334-1B and 334-2B in the archform 316, then, are defined in a Y-axis (e.g., within 2 mm from the origin of the archform basis). The archform align points 334-1B and 334-2B can be computed by getting the crown center of the tooth 364, finding the closest point in the archform 316, constructing the arch basis in the archform 316 in the closest point, and computing the respective archform align point.

To move the tooth 364 from the first position 350-1 to the second position 350-2 corresponding to the archform 316, the occlusal point, the align points 334, and the root center 333 can be used to compute the transformation (R,T), which can be based on optimization of the object function of each point's movement:

$$J = \sum_{i=1}^{N} \|w_i(RP_i + T - Q_i)\|^2,$$

where $P_i$ is the first position 350-1, $Q_i$ is the second position 350-2, and $w_i$ is the weight of the movement. Larger weights can force $P_i$ and $Q_i$ to be closer.

In some embodiments, the align points 334-1A and 334-1B can be moved to the archform 316 and the root center 333 can be kept close to its first position 333-1 while the weight of movement for the root center 333 is set relatively low (e.g., 0.1~0.2) such that it can be moved more freely to promote accurate alignment of the align points 334 to the archform 316. Then, the root center 333 can be pulled to the same level of the first position 333-1, while the weight of movement of the root center 333 is increased (e.g., 0.5~5.0) depending on the type of tooth 364, where a larger weight is used for teeth that are not desired to have much intrusion and/or extrusion, such as molars.

However, even after alignment with the archform 316, additional adjustment of the tooth 364 may still be desired. For example, tooth angulation may be set within a normal range based on a doctor's prescription or protocol, upper lateral incisors may be leveled, and/or a tooth 364 may be manually adjusted to improve alignment, among others. To provide for such adjustment, the align points 334 in the archform 316 can be adjusted to change a relative position of the tooth 364. Such changes can be performed manually and/or automatically.

Figure 4:
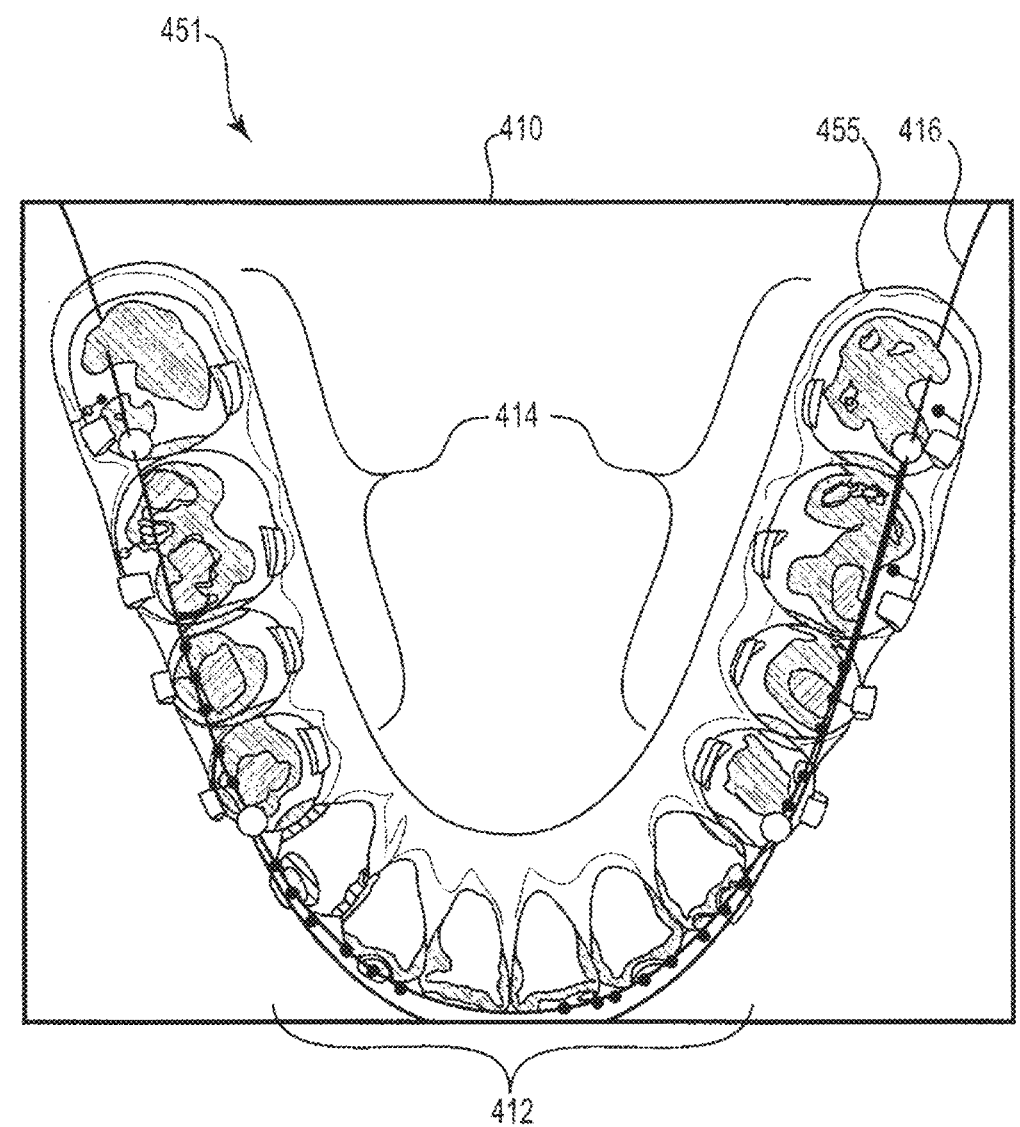
FIG. 4 illustrates an occlusogram of a virtual dental model of a jaw according to one or more embodiments of the present disclosure.
Figure 4:
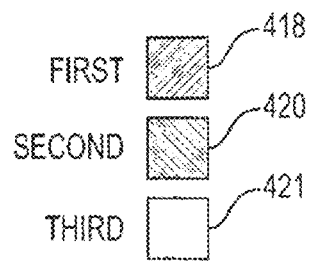

FIG. 4 illustrates an occlusogram 410 of a virtual dental model 451 of a jaw 455 according to one or more embodiments of the present disclosure. Treatment plans including the use of virtual dental modeling can more heavily weight alignment for occlusion of the anterior teeth 412 while more heavily weighting contact and collision for occlusion of the posterior teeth 414. Anterior teeth 412 can include incisors and canines, while posterior teeth 414 can include premolars and molars. Alignment of posterior teeth 414 into an archform 416 (e.g., according to a treatment plan) can provide a good initial corrected position for the posterior teeth 414, but contact and collision problems may remain.

To promote visualization of such contact and collision problems, an occlusogram 410 can be created. Collision and occlusal regions between teeth of an upper jaw and a lower jaw of a virtual dental model can be computed and color coded. In some instances, a collision (e.g., a collision region) can be defined as a mesh vertex from one tooth (e.g., a posterior tooth) of one of an upper jaw and a lower jaw being inside a tooth from the opposite jaw, as described herein. An occlusal region can include a mesh vertex from one tooth (e.g., a posterior tooth) of one of the upper jaw and the lower jaw being within a threshold distance from another tooth of the opposite jaw. A space region can include a mesh vertex from one tooth (e.g., a posterior tooth) of one of the upper jaw and the lower jaw being outside the threshold distance from the other tooth of the opposite jaw.

Figure 5:
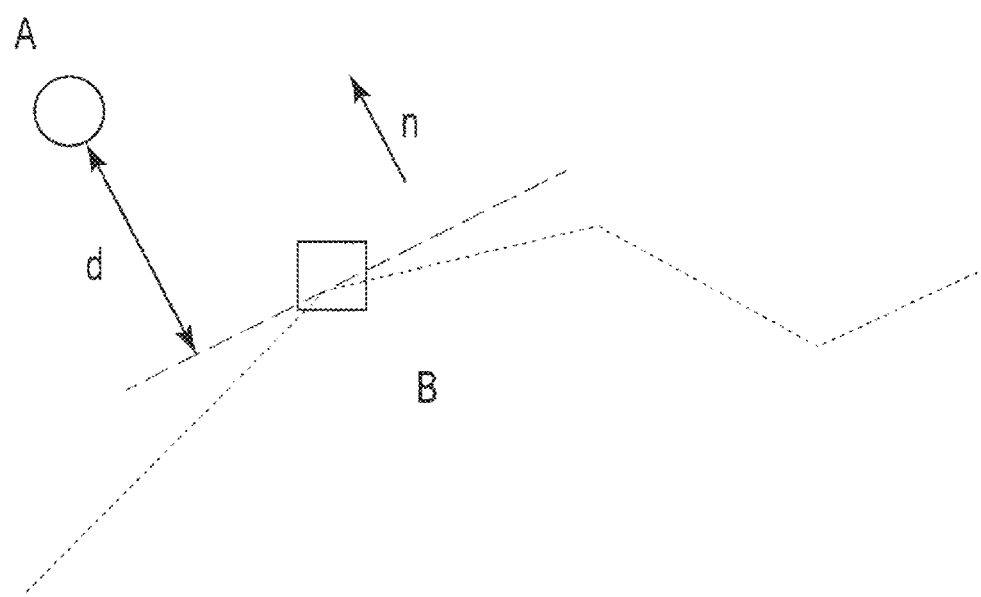
FIG. 5 is a diagram illustrating point to mesh distance according to one or more embodiments of the present disclosure.

FIG. 5 is a diagram illustrating point to mesh distance according to one or more embodiments of the present disclosure. As described herein, each tooth in a virtual dental model can be represented by a mesh (e.g., a closed mesh). Each vertex in the mesh for a particular tooth can have a normal assigned to it (e.g., an average normal of triangles linked to the vertex, where the mesh is a triangular mesh).

A distance (d) can be computed from a particular vertex point (A) to a nearest point in the mesh (B) in the direction of the normal (n) for the point A. If d<0 (or some small value such as 0.1 millimeter (mm) or −0.1 mm), A is inside the mesh and it's in a collision region. Points in collision regions can be displayed in a first color (e.g., red, as represented by first hatching 418 in FIG. 4). If $d_c$>d>0, A is outside the mesh and in an occlusal region, where $d_c$ is a control distance having a value that can be set to a distance defining a boundary between what is considered an occlusal region and a space region (e.g., 1 mm). Points in occlusal regions can be displayed in a second color (e.g., green, as represented by second hatching 420 in FIG. 4). If d>$d_c$, then A is in a space region. Points in space regions can be displayed in a third color (e.g., white, as represented by third hatching 421 in FIG. 4). In some embodiments, additional regions can be defined, such as an intermediate region between collision and occlusal regions, which can be displayed in a fourth color (e.g., yellow, not specifically illustrated in FIG. 4).

A collision region is an area that includes vertices in a mesh of a first tooth that are inside the mesh of a second tooth (e.g., a first tooth of an upper jaw and a second tooth of a lower jaw). Collisions between teeth in a virtual dental model may be undesirable because they cannot exist with physical teeth (e.g., one tooth cannot be inside of another tooth). Furthermore, collisions included in a virtual dental model representing a stage in a treatment (e.g., a final stage) may only be resolved, in some instances, by removing some enamel of a tooth, for example, by IPR.

An occlusal region is an area that includes vertices in a mesh of a first tooth that are close to vertices in a mesh of a second tooth (e.g., a first tooth of an upper jaw and a second tooth of a lower jaw). For posterior teeth, it can be desirable to maximize the occlusal region for better grind and chew functionality.

Figure 6:
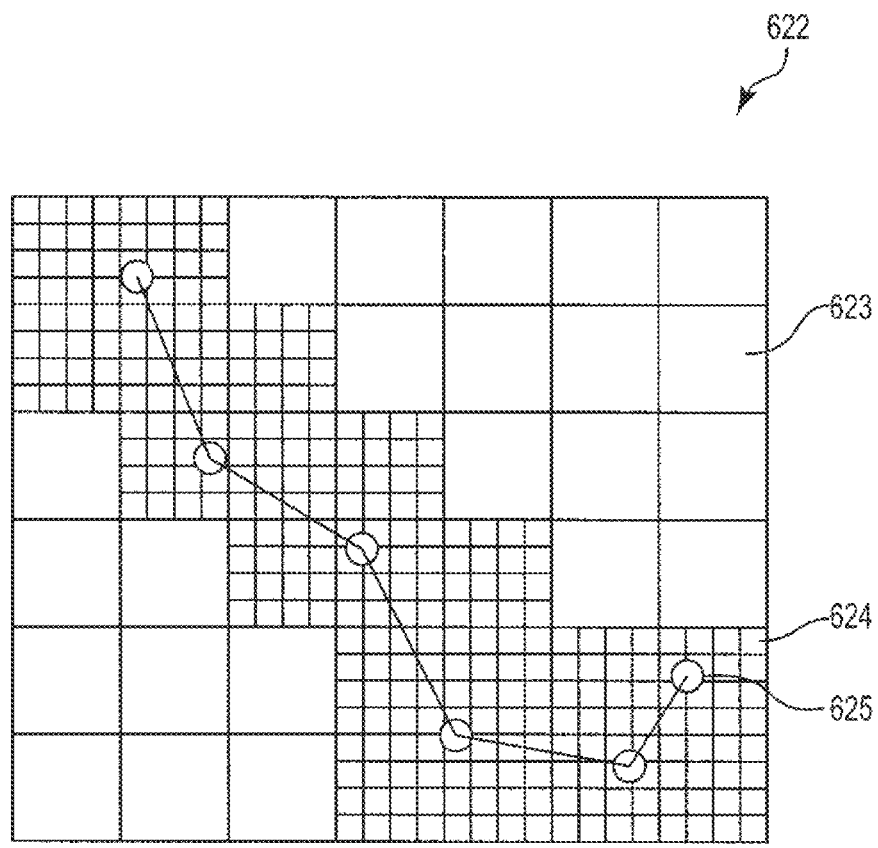
FIG. 6 illustrates a map of points in a virtual dental model according to one or more embodiments of the present disclosure.

FIG. 6 illustrates a map of points in a virtual dental model according to one or more embodiments of the present disclosure. Before a distance (d) can be computed from a particular vertex point (A) to a nearest point in the mesh (B) in the direction of the normal (n) for the point A, a determination needs to be made as to what the nearest point is. A basic idea of many nearest point searches is to organize scattered vertices in space in such a way that for each search, only a small number of comparisons is needed (e.g., rather than comparing distances between a particular point and all other points in the mesh). In contrast, one or more embodiments of the present disclosure can store the closest vertex for each point in the neighborhood of the model. Given a particular 3D point, a closest vertex can then immediately be found. In order to reduce an amount of memory used with such embodiments, a coarse to fine approach can be used.

First, a bounding box 622 that is at least bigger than a tight bounding box of a number of vertices in the model can be found. The bounding box can be divided (e.g., uniformly divided) into many rectangles (boxes in 3D) called coarse boxes (e.g., coarse box 623). However, when a particular box is near a vertex in the model, it can be subdivided into even smaller boxes (e.g., fine boxes, such as fine box 624). For each box, the closest vertex to the center of the box can be stored (e.g., such as vertex 625).

For points other than box centers, there may be an error in the distance to the closest vertex of the mesh since every box stores only the closest vertex to its center. However, the coarse box is far from the model, so the error is small compared to the distance to the vertex. For the fine box, its size is small enough so that the error is also small compared to the distance. This tradeoff between accuracy and the amount of data stored can be beneficial to promote fast searches for a closest mesh vertex pair.

In some embodiments, determining a plurality of closest mesh vertex pairs can include bounding a virtual dental model with a first box and dividing the first box into a plurality of coarse boxes. Those of the plurality of coarse boxes that are near a mesh vertex can be subdivided into a plurality of fine boxes. A closest mesh vertex can be stored for each of the plurality of coarse boxes and each of the plurality of fine boxes. By reference to the stored closest mesh vertex, the plurality of closest mesh vertex pairs for a posterior tooth of the upper jaw and the corresponding posterior tooth of the lower jaw can be determined.

In various embodiments, determining a plurality of closest mesh vertex pairs can include bounding a virtual dental model with a first box and dividing the first box into a plurality of coarse boxes. A set of neighboring coarse boxes for a particular mesh vertex can be found and the particular mesh vertex can be stored as a closest mesh vertex for those of the neighboring coarse boxes that do not have a stored closest mesh vertex. The set of neighboring coarse boxes can be subdivided into a plurality of fine boxes. The particular mesh vertex can be stored as a closest mesh vertex for those of the plurality of fine boxes that were subdivided from coarse boxes having a stored closest mesh vertex that is the particular mesh vertex. By reference to the stored closest mesh vertex, the plurality of closest mesh vertex pairs for a posterior tooth of the upper jaw and the corresponding posterior tooth of the lower jaw can be determined.

In a number of embodiments, determining a plurality of closest mesh vertex pairs can include bounding a virtual dental model with a first box, dividing the first box into a plurality of coarse boxes, and, for a particular vertex, setting a reference to a closest vertex as null. For each vertex in the model, neighboring coarse boxes can be found. For those coarse boxes having no reference to a closest vertex (e.g., null), the reference can be set to the current vertex, otherwise the new closest vertex to the box can be found. The coarse boxes closest to the particular vertex can be subdivided into fine boxes and the fine boxes can be filled with references to a new closest vertex.

Thus, according to a number of embodiments of the present disclosure, determining a plurality of closest mesh vertex pairs can be achieved by making only a small number of comparisons (e.g., as opposed to comparing all or most vertices in a model). Using a k-dimensional tree (k-d tree) as a space partitioning data structure for organizing points in k-dimensional space and/or an octree (e.g., a tree data structure in which each internal node has eight children) may be relatively fast alternative approaches for a closest mesh vertex pair search. However, the relatively processing-intensive requirements of computation of collision and occlusion in the virtual dental models of the present disclosure make an even less processing-intensive (e.g., faster) approach to closest mesh vertex pair search, such as those described herein, advantageous.

Figure 7:
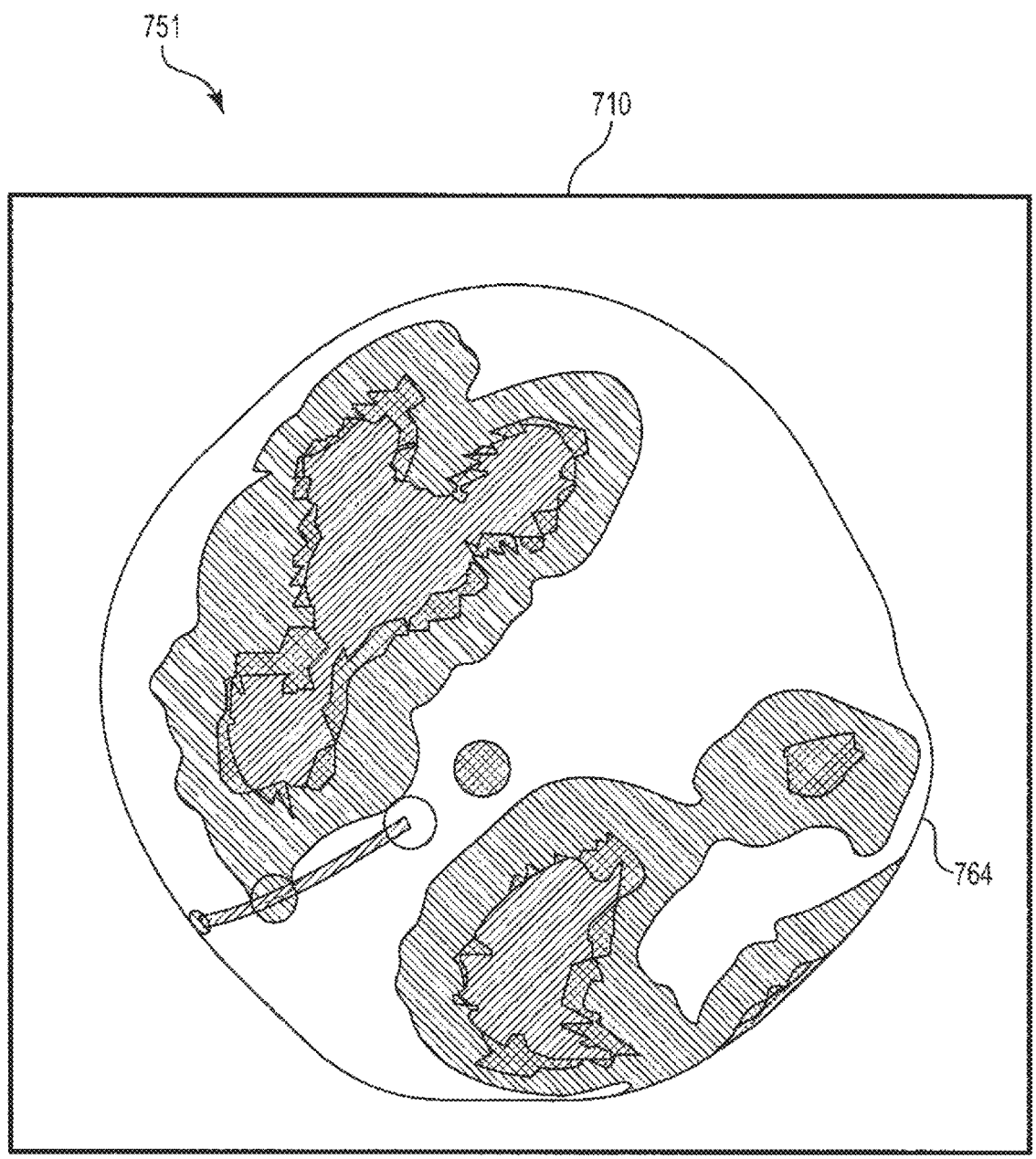
FIG. 7 illustrates an occlusogram of a virtual dental model of a tooth according to one or more embodiments of the present disclosure.
Figure 7:
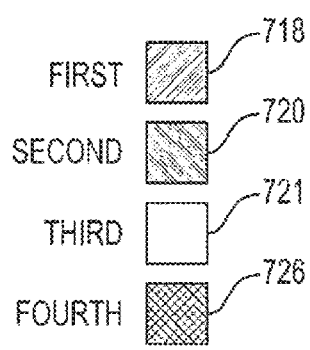

FIG. 7 illustrates an occlusogram 710 of a virtual dental model 751 of a tooth 764 according to one or more embodiments of the present disclosure. Once the point-mesh distance has been determined, such distances can be color coded for display to a user as described herein. For example, for a vertex with distance d, the color can be defined as: d≤−0.1 mm, color=first color (e.g., red, as indicated by first hatching 718); 0.1 mm<d≤0.1 mm, color=fourth color (e.g., yellow, as indicated by fourth hatching 726); 0.1 mm<d≤1 mm, color=second color (e.g., green, as indicated by second hatching 720); d>1 mm, color=third color (e.g., white, as indicated by third hatching 721).

Figure 8:
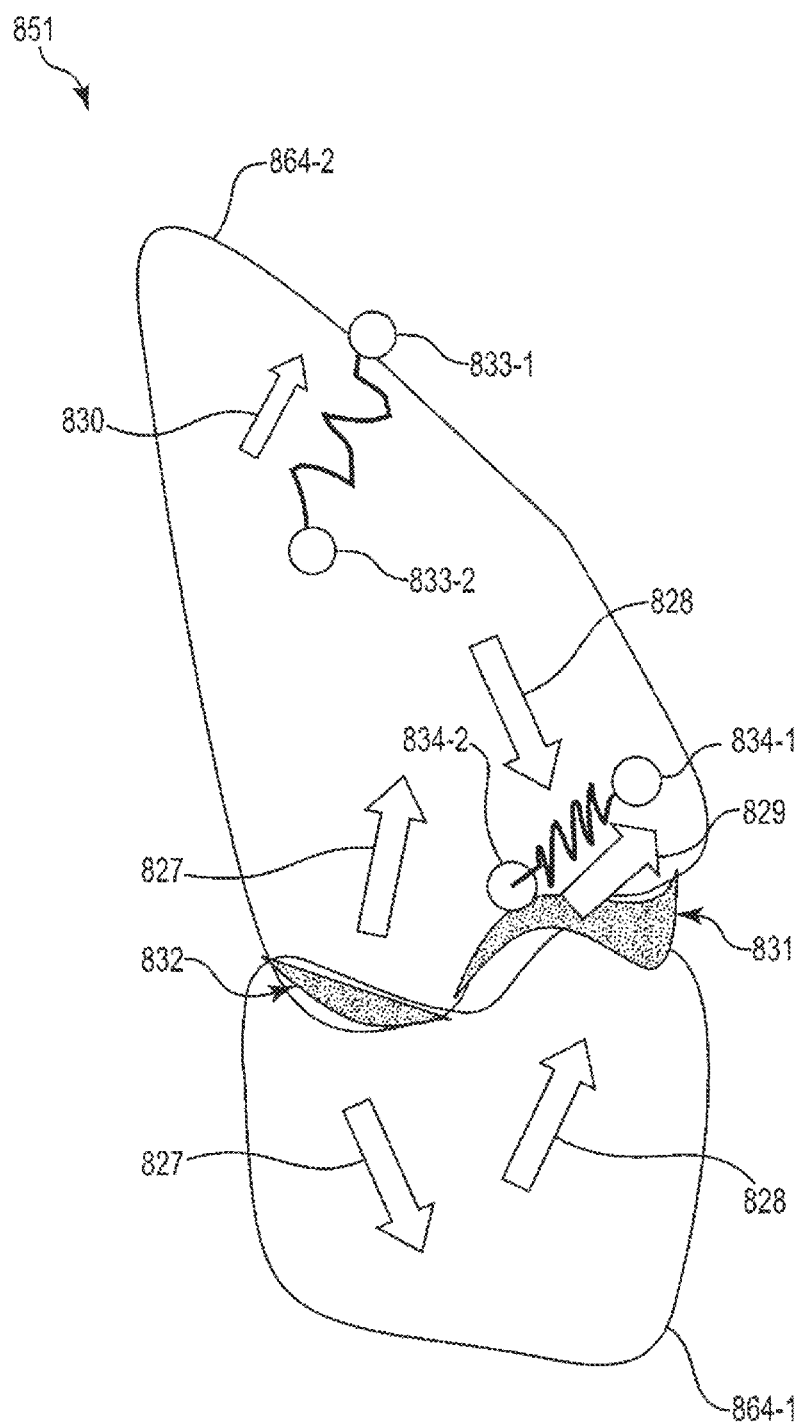
FIG. 8 illustrates a virtual dental model including two teeth with a number of forces acting thereon during a biting simulation according to one or more embodiments of the present disclosure.

FIG. 8 illustrates a virtual dental model 851 including two teeth 864-1, 864-2 with a number of forces acting thereon during a biting simulation according to one or more embodiments of the present disclosure. According to a number of embodiments of the present disclosure, a biting simulation can be used to improve posterior occlusion. An analogy can be drawn between the biting simulation and a force model such that a tooth can be moved (e.g., translated and/or rotated) by the forces created by a collision, space, and/or other reasons. While a force model is described herein to illustrate various features of the present disclosure and to promote understanding, some embodiments of the present disclosure perform a biting simulation without modeling forces (e.g., the biting simulation is implemented by directly optimizing an energy function that evaluates the collision, space, root movement, and/or alignments, as described herein).

A biting simulation can include simulating how a first jaw and a second jaw (e.g., an upper and lower jaw) of a virtual dental model fit together in respective orientations that model how physical teeth of a patient's jaws would fit together in a bite position. The biting simulation can be performed between two jaws of a virtual dental model collectively (e.g., such that the simulation is performed in consideration of all of the teeth of the virtual dental model substantially simultaneously), or individually between corresponding teeth in a first jaw and a second jaw of the virtual dental model (e.g., such that the simulation is performed successively for a corresponding tooth of a first jaw and a corresponding tooth of a second jaw until the simulation has been performed for a sufficient amount of the teeth in the jaws to return a result with a desired amount of certainty and/or accuracy, etc.). Goals of a biting simulation can include resolving collisions between corresponding teeth of the upper and lower jaws, closing posterior space between corresponding teeth of the upper and lower jaws, and/or achieving a better ridge-groove relationship between teeth of the upper and lower jaws (e.g., so that ridges of teeth of a first jaw fit nicely into the groove between teeth of a second jaw), among others.

Some examples of forces that can be applied to a number of teeth in the virtual dental model 851 during the biting simulation include collision 827, space 828, alignment 829, and root 830, among others. If there is a collision 832 between one vertex of a first tooth 864-1 and a second tooth 864-2 (e.g., a vertex in a lower tooth with a corresponding upper tooth), an amount of force 827 (e.g., a relatively small amount of force) can be created to push the first tooth 864-1 and the second tooth 864-2 apart. In some embodiments, the teeth of the virtual dental model 851 can be "hard" such that any force of collision 827 would have a greater magnitude than the other forces. However, during the biting simulation, the hardness of the teeth can be variable to help achieve a better occlusion. For example, at the beginning of the biting simulation, the collision force 827 can be set to a relatively small magnitude so that the tooth is modeled as being "soft" like a rubber that can be compressed to help promote a greater contact region between teeth in the virtual dental model. As the biting simulation progresses, the hardness of the teeth can be increased to result in an increased repulsive force of collision 827 to help remove collisions 832 between teeth of the first and the second jaw in the virtual dental model 851. In some embodiments, the hardness of the teeth (e.g., posterior teeth) can be increased according to a number of iterations of the biting simulation, can be increased manually by a user, and/or can be increased according to some other metric If there is space 831 between a vertex of the first tooth 864-1 and the second tooth 864-2, a space force 828 can be created to pull the first tooth 864-1 and the second tooth 864-2 closer together. Align forces 829 can be created to pull an align point from its current position 834-2 to an initial position 834-1 in a treatment planned archform (e.g., archform 416 illustrated in FIG. 4) to retain the alignment of a first jaw and/or a second jaw (e.g., where a number of teeth in the virtual dental model 851 have been aligned to the treatment planned archform prior to the biting simulation). A root force 830 can be created to pull a root of a tooth 864-2 back to its initial position 833-1 from its current position 833-2 to simulate the difficulty of moving a root of a physical tooth. Other forces can include photo attraction forces, as described herein and axial forces (e.g., simulated gravity), among others.

As described herein, the biting simulation can operate according to an energy function. The optimization (e.g., minimization) of the energy function can create a stable solution for the system (e.g., the virtual dental model). In a stable solution, all "forces" can be balanced with each other.

For each posterior tooth in a first jaw, vertex pairs can be detected. For each vertex in the occlusal surface of a particular posterior tooth in the first jaw, the nearest vertex pair to the second jaw can be detected as $(C_i, D_i)$, where $C_i$ is a point in the tooth in the first jaw and $D_i$ is a point in a corresponding tooth in the second jaw. The midpoint is $E_i=(C_i+D_i)/2$. $(C_i, D_i)$ can be added into a vertex pair list for the tooth in the first jaw and $(E_i, D_i)$ can be added into a vertex pair list for the corresponding tooth in the second jaw. The distance between the vertex pairs can be computed, and if it is less than zero, then the vertex can be considered to be in collision. If the distance is greater than zero, but less than $d_c$ (e.g., 1 mm), then the vertex can be considered to be in space. If the distance is greater than $d_c$, then the vertex may be disregarded for the computation of forces. After the distance determination, the current root position and initial position before biting simulation can be computed. The current align position and initial position before the biting simulation can also be computed.

The following energy function can be constructed for teeth (e.g., every tooth) in the first jaw and in the second jaw:

$$J = w_c \sum_{i=1}^{N_c} \|R*C_i + T - E_i\|^2 + w_s \sum_{i=1}^{N_s} \|R*C_i + T - E_i\|^2 + w_r*N_p*\|R*C_r + T - E_r\|^2 + w_a*N_p*\sum_{i=1}^{N_a} \|R*C_i + T - E_i\|^2$$

Where:
$N_c$ is the number of vertices in collision;
$w_c$ is the weight of collision energy;
$N_s$ is the number of vertices in space;
$w_c$ is the weight of space energy;
$N_p = N_c + N_p$ is the number of vertices in occlusal;
$w_r$ is the weight of root movement energy;
$w_a$ is the weight of alignment (e.g., align points) movement energy; and
(R,T) is the rotation and translation of the tooth transform.

The transformation of the tooth can be directly computed by optimizing the energy function. After the tooth has moved to a new position according to the optimization of the energy function, IPR can be computed to fit the setup. The transition from "soft" to "hard" collisions, as described herein, can include changing the weight of the collision (e.g., $w_c$).

Accordingly, an algorithm for the same can include:
(1) detecting vertex pairs of collision, space, root, and alignment;
(2) setting the weight of collision as:
  a. for iterations<a first number (e.g., 10), the weight of collision is set at a first value (e.g., 30);
  b. else, if the iteration<a second number (e.g., 20), the weight is increased by the first value (e.g., 30) every iteration;
  c. the weight is then increased by a second value (e.g., 200) every iteration;
(3) minimizing the energy function to get tooth movement (R,T);
(4) setting up IPR based on the configuration; and
(5) repeating steps 1-4 until a certain number of iterations is reached.

Figure 9:
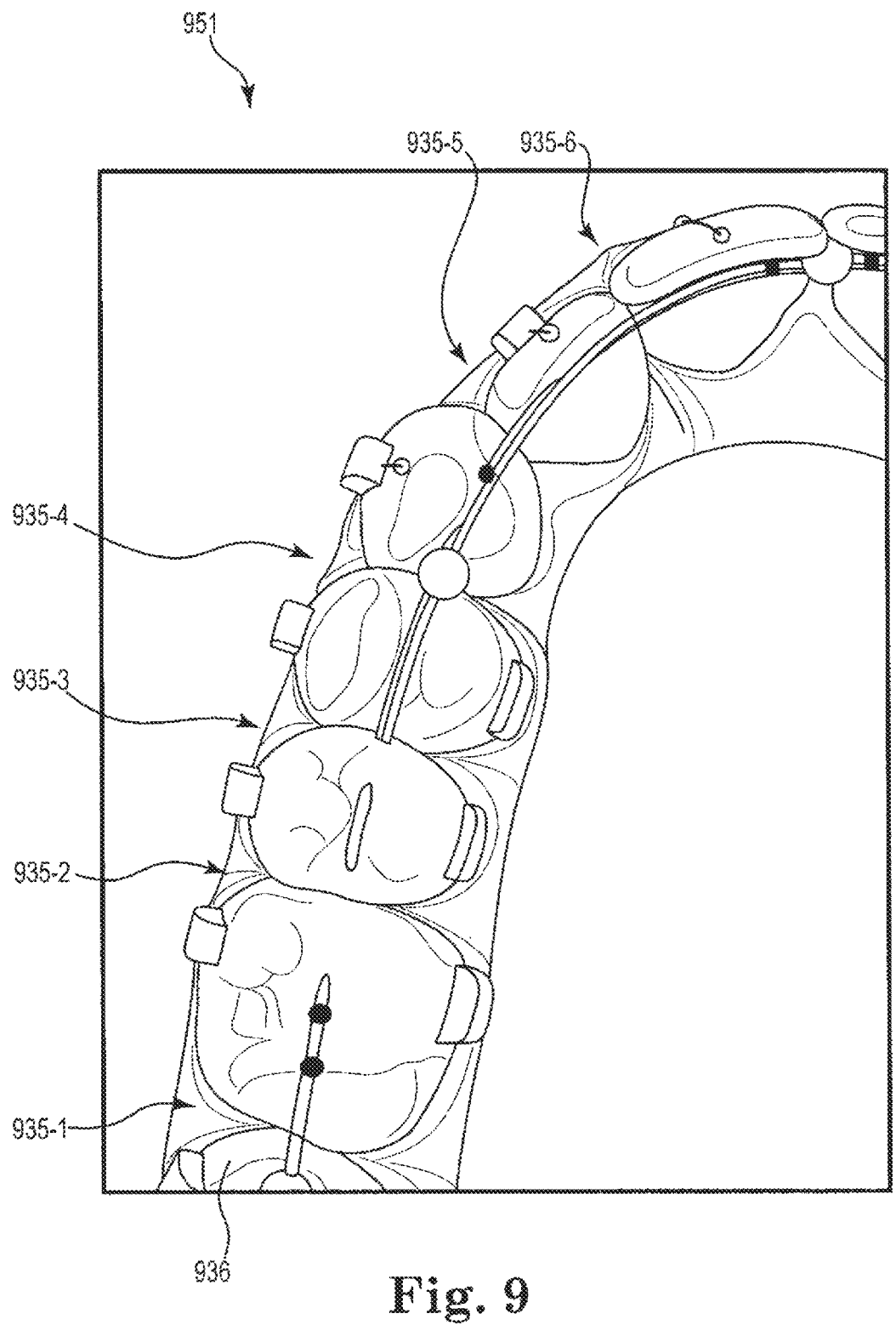
FIG. 9 illustrates a virtual dental model including crowding between teeth according to one or more embodiments of the present disclosure.

FIG. 9 illustrates a virtual dental model 951 including crowding between teeth according to one or more embodiments of the present disclosure. After teeth are aligned in an archform of a particular jaw, crowding between adjacent teeth in the jaw may be resolved by moving one or more teeth along the archform, by IPR, and/or by adjustment of the archform. According to a number of embodiments of the present disclosure, three types of teeth may be defined in a virtual dental model: non-movable, anchorage, and normal.

A tooth that has been defined as non-movable is not allowed to move. Examples of such teeth can include a pontic, a crown, a bridge, and a partially erupted tooth, among others.

A tooth that has been defined as an anchorage can be moved manually (e.g., by an operator of a user interface for the virtual dental model). Such a tooth may not automatically follow adjustments to the jaw (e.g., to the archform).

A tooth that has been defined as normal can be moved freely and may automatically follow adjustments to the jaw (e.g., to the archform). For example, anterior teeth may be defined as normal.

In some instances, there may be a physical limit to the amount of IPR that can be applied to a physical tooth. Furthermore, it may be physically easier to apply IPR to anterior teeth as opposed to posterior teeth. Considering the factors described herein, a cost function can be optimized to solve mobility, space, IPR, and/or midline considerations. Midline can refer to a middle line between two central incisors and midline shift can refer to a distance that a point on the midline shifts after the teeth have been adjusted (e.g., either physically or in the virtual dental model). The cost function can include parameters of intra-arch setup for at least one of the upper jaw and the lower jaw. For example, the cost function can be:

$$K = \sum_{i=1}^{\#} w_i z_i^2 + \sum_{i=1}^{\#-1} g_i(s_i - z_i + z_{i+1} - t_i)^2 + h(l + z_{k+1} - z_k - r)^2$$

Where:
# is the number of the tooth;
$w_i$ is the weight of tooth movement;
$z_i$ is the movement of tooth i to next tooth along the archform;

$g_i$ is the weight of space/IPR between tooth i and i+1;
$s_i$ is the current space/IPR for tooth i;
$t_i$ is the space/IPR assigned between tooth i and i+1;
$s_i-z_i+z_{i+1}$ is the space/IPR after the tooth is moved;
h is the weight of midline shift;
l is the current midline shift;
r is the setup value of midline shift; and
$z_k, z_{k+1}$ are the movement of two middle incisors.

In general, greater weights indicate that the parameter will be complied with more, while lesser weights mean that the parameter is less stringent on the overall outcome. If a particular weight is infinitely large, the corresponding parameter must be set to the assigned value. If the weight is zero, the corresponding parameter can be set to any value or free to change.

For example with respect to tooth mobility, the weights can be set to $w_i=0.01$, if the tooth is free to move or $w_i=1,000,000$ if the tooth is not movable or is an anchorage. For example with respect to space/IPR:

- $g_i$ can be set to 10,000 and $t_i$ can be set to −0.1 if there is contact (e.g., 0.1 mm overlap between the teeth);
- $g_i$ can be set to 10,000 and $t_i$ can be set to 2.0 if there is 2 mm left for this contact;
- $g_i$ can be set to 10,000 and $t_i$ can be set to −0.75 if there is a 0.75 mm IPR assigned;
- $g_i$ can be set to 1 and $t_i$ can be set to 0.0 if normal space and/or IPR can be assigned;
- $g_i$ can be set to 0.5 and $t_i$ can be set to 0.0 if more normal space and/or IPR an be assigned; or
- $g_i$ can be set to 0.25 and $t_i$ can be set to 0.0 if a maximum amount of space and/or IPR is allowed.

For example with respect to midline shift, h can be set to 10,000 and r can be set to 2.0 if the midline shift is set to 2 mm or h can be set to 0.000001 if the midline shift is not set and/or is free to change. The above examples can be combined to implement a number of different setups and/or algorithms.

An example of automatic IPR setup can include setting the last molars as anchorages, while other teeth are free to move. If there is any space between teeth, all teeth can be set to contact (e.g., leaving 0.1 mm overlap between two teeth) and the space assigned to the mesial side of the canine can be set by $g_i=0.25$ and $t_i=0.0$. If the total IPR is between 0 and 0.8 mm, the IPR can be assigned to the mesial side of the canine by a greater amount, such as $g_i=0.25$ and $t_i=0.0$, and between incisors by a lesser amount, such as $g_i=1.0$ and $t_i=0.0$. If the total IPR is greater than 0.8 mm, the IPR can be assigned to the canine, incisors, and premolars by $g_i=0.25$ and $t_i=0.0$, $g_i=0.5$ and $t_i=0.0$, and $g_i=1.0$ and $t_i=0.0$, respectively.

For example, in FIG. 9, the last molar 936 can be set as an anchorage. The total IPR for this virtual dental model 951 is 2.96 mm, which is greater than 0.8 mm, therefore IPR can be assigned to the canine, incisors, premolars, and molars. An example result of optimizing the function can result in IPR values assigned as: 0.00 mm between the last molar and an adjacent molar as indicated by IPR 935-1, 0.60 mm between two molars and between a premolar and molar as indicated respectively by IPR 935-2 and IPR 935-3, 1.00 mm between the premolars as indicated by IPR 935-4, and 0.38 mm between the canine and premolar and between the incisor and canine as indicated respectively by IPR 935-5 and IPR 935-6.

Once IPR values have been assigned in the virtual dental model, the teeth can be adjusted in the archform accordingly. Because movement in the archform may alter the spacing and/or crowding between adjacent teeth, several iterations of optimization of the function may be performed to reach a stable and/or desirable result. Such iterations may include computing space, crowding, and midline shift, optimizing the function to adjust the teeth, moving the teeth in the archform for a certain percentage (e.g., 90%) of the result computed from optimizing the function, and repeating the process until the amount of movement and/or IPR for each tooth is within specified thresholds of acceptability. In some embodiments, for a particular tooth, IPR can be assigned to one side of the tooth, while any spacing is closed for the other side of the tooth. In various embodiments, IPR can be computed for portions of a posterior tooth that has collisions remaining after the adjustment according to a last iteration.

Figure 10:
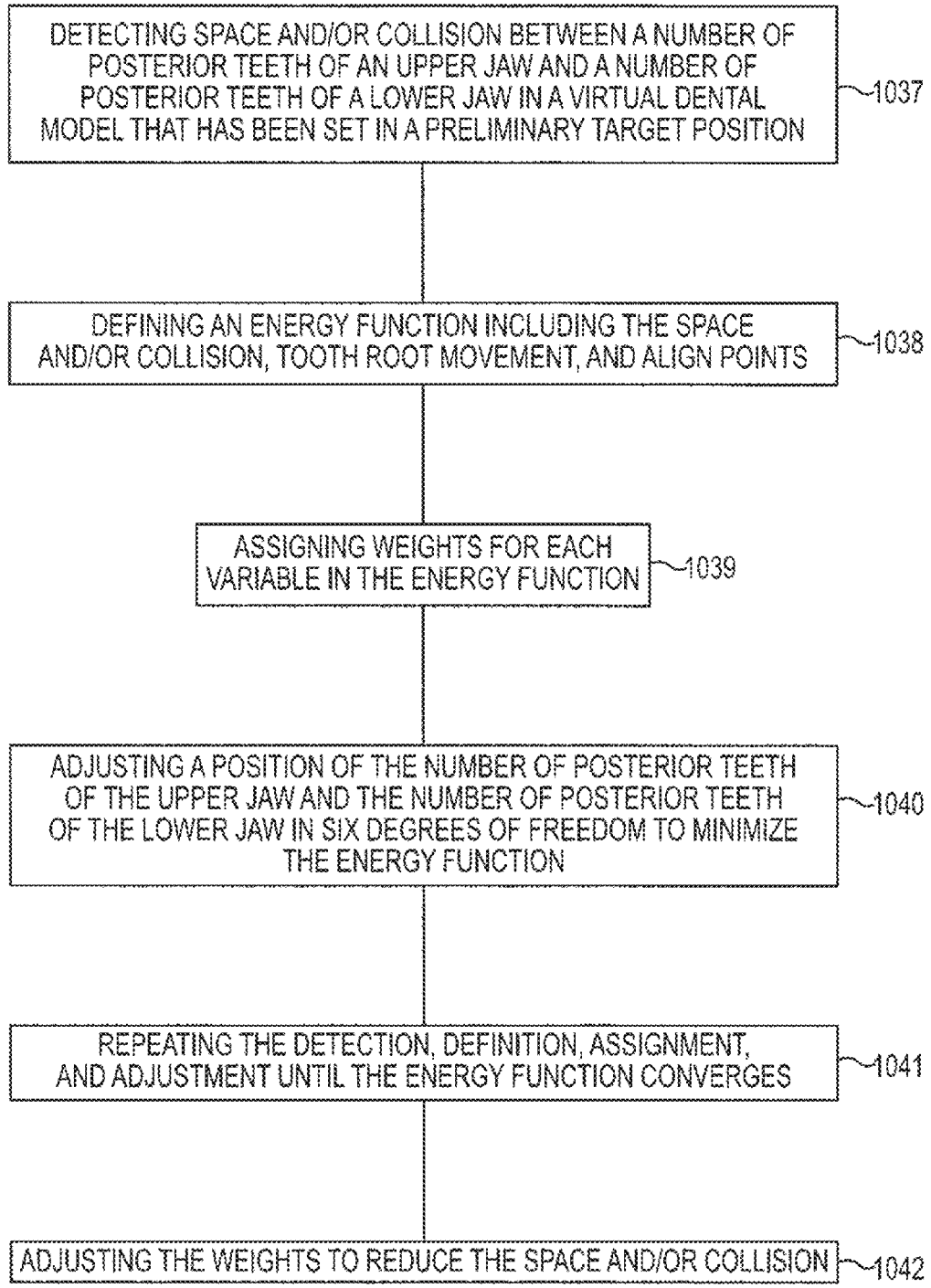
FIG. 10 is a flow chart illustrating a method for adjustment of tooth position in a virtual dental model according to one or more embodiments of the present disclosure.

FIG. 10 is a flow chart illustrating a method for adjustment of tooth position in a virtual dental model according to one or more embodiments of the present disclosure. At 1037 the method can include detecting space and/or collision between a number of posterior teeth of an upper jaw and a number of posterior teeth of a lower jaw in a virtual dental model that has been set in a preliminary target position. In some embodiments, the preliminary target position can be manually defined by a user. In a number of embodiments, the preliminary target position can be automatically defined by the computing device.

At 1038 the method can include defining an energy function including the space and/or collision, tooth root movement, and align points. At 1039 the method can include assigning weights for each variable in the energy function. An example of an energy function and accompanying assignment of weights is described above with respect to FIG. 8. At 1040 the method can include adjusting a position of the number of posterior teeth of the upper jaw and the number of posterior teeth of the lower jaw in six degrees of freedom to minimize the energy function.

At 1041 the method can include repeating the detection, definition, assignment, and adjustment until the energy function converges. At 1042 the method can include adjusting the weights (e.g., after the energy function converges) to reduce the space and/or collision.

In some embodiments, the position of the teeth after convergence of the energy function and/or adjustment of the weights can be defined as the final target position. In a number of embodiments, a user can manually adjust the position of a number of teeth after the energy function converges to further refine the occlusion. Such embodiments may provide advantages over some previous approaches by reducing the amount of manual adjustment required to achieve a desired final target position. In such embodiments, the position after convergence and manual adjustment can be defined as the final target position.

The method can include defining a number of treatment steps between the preliminary target position and a final target position for each of the upper jaw and the lower jaw based on the converged energy function, wherein each of the number of treatment steps corresponds to an amount of adjustment to be performed by an orthodontic appliance. A series of incremental dental position adjustment appliances can be designed to correspond to the number of treatment steps (e.g., automatically by software).

Figure 11:
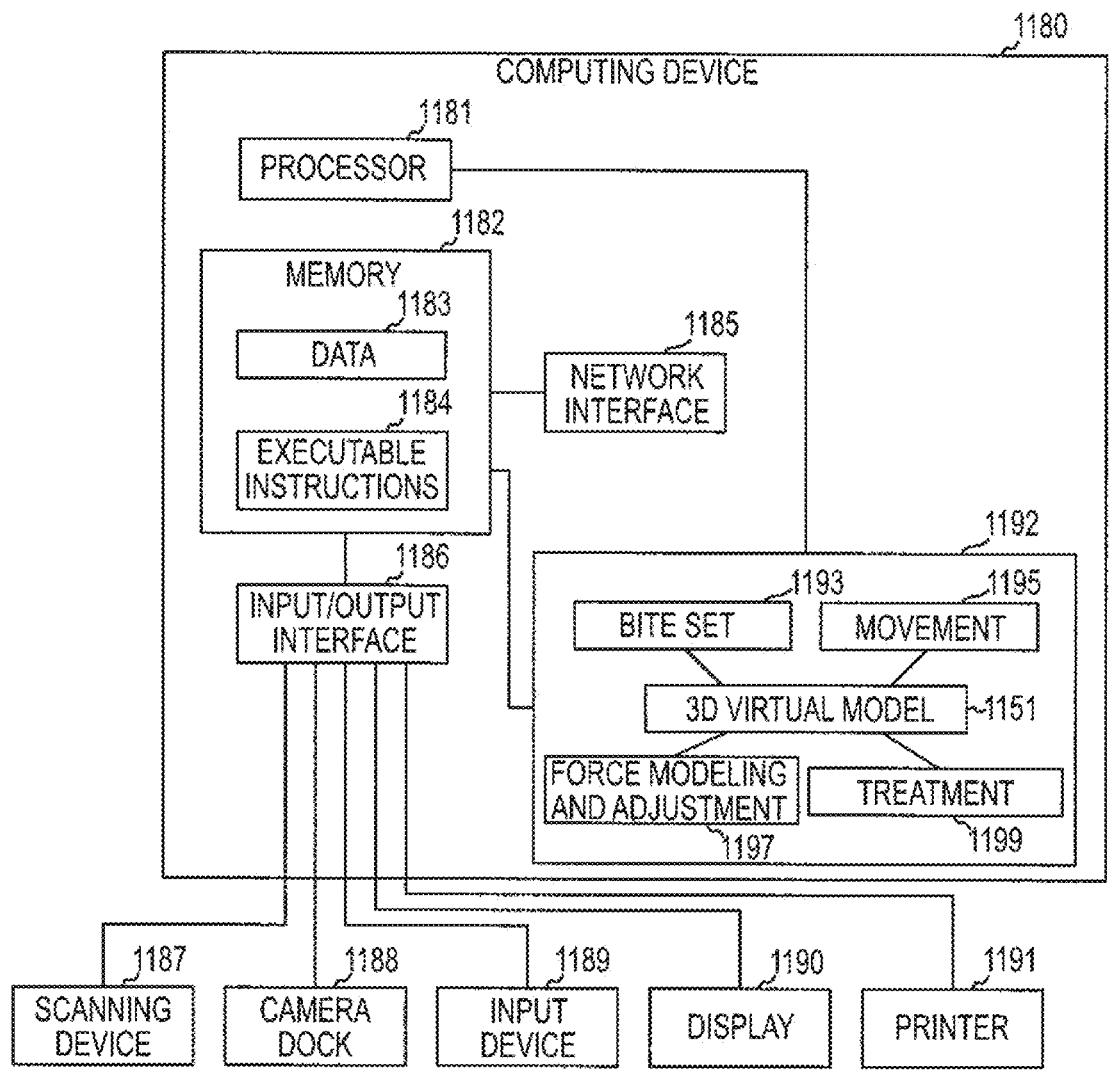
FIG. 11 illustrates a system for adjustment of tooth position in a virtual dental model according to one or more embodiments of the present disclosure.

FIG. 11 illustrates a system for adjustment of tooth position in a virtual dental model according to one or more embodiments of the present disclosure. In the system illustrated in FIG. 11, the system includes a computing device 1180 having a number of components coupled thereto. The computing device 1180 includes a processor 1181 and memory 1182. The memory can include various types of information including data 1183 and executable instructions 1184 as discussed herein.

Memory and/or the processor may be located on the computing device 1180 or off the device in some embodiments. As such, as illustrated in the embodiment of FIG. 11, a system can include a network interface 1185. Such an interface can allow for processing on another networked computing device or such devices can be used to obtain information about the patient or executable instructions for use with various embodiments provided herein.

As illustrated in the embodiment of FIG. 11, a system can include one or more input and/or output interfaces 1186. Such interfaces can be used to connect the computing device with one or more input or output devices.

For example, in the embodiment illustrated in FIG. 11, the system includes connectivity to a scanning device 1187, a camera dock 1188, an input device 1189 (e.g., a keyboard, mouse, etc.), a display device 1190 (e.g., a monitor), and a printer 1191. The input/output interface 1186 can receive data, storable in the data storage device (e.g., memory 1182), representing the virtual dental model 1151 corresponding to the patient's upper jaw and the patient's lower jaw.

In some embodiments, the scanning device 1187 can be configured to scan a physical mold of a patient's upper jaw and a physical mold of a patient's lower jaw. In one or more embodiments, the scanning device 1187 can be configured to scan the patient's upper and/or lower jaws directly.

The camera dock 1188 can receive an input from an imaging device (e.g., a 2D imaging device) such as a digital camera or a printed photograph scanner. The input from the imaging device can be stored in the data storage device 1182.

The processor 1181 can be configured to provide a visual indication of a virtual dental model 1151 on the display 1190 (e.g., on a GUI running on the processor 1181 and visible on the display 1190).

Such connectivity can allow for the input and/or output of virtual dental model information or instructions (e.g., input via keyboard) among other types of information. Although some embodiments may be distributed among various computing devices within one or more networks, such systems as illustrated in FIG. 11 can be beneficial in allowing for the capture, calculation, and/or analysis of information discussed herein.

The processor 1181, in association with the data storage device 1182, can be associated with data and/or application modules 1192. The processor 1181, in association with the data storage device 1182, can store and/or utilize data and/or execute instructions to provide a number of application modules for virtual dental modeling.

Such data can include the 3D virtual dental model 1151 described herein (e.g., including a first jaw and a second jaw). Such application modules can include a bite set module 1193, a movement module 1195, a force modeling and adjustment module 1197, and/or a treatment module 1199.

The bite set module 1193 can be configured to bite set a first jaw and a second jaw in the virtual dental model 1151. The movement module 1195 can be configured to move the first jaw toward the second jaw in the virtual dental model 1151 from the bite set position (e.g., to set the teeth in respectively close positions under the influence of collision forces similar to a chewing process). If the teeth are not inconsistent and/or misaligned, the pressure should be distributed with some degree of uniformity across the teeth. However, if there are inconsistent and/or misaligned teeth, there may be a less uniform distribution of pressure.

The force modeling and adjustment module 1197 can be configured to model a number of repulsive forces for collisions between a number of points in the first jaw and a respective number of points in the second jaw in the virtual dental model 1151. The repulsive forces can be modeled in response to the first jaw being moved toward the second jaw from the bite set position (e.g., in response to the jaws having increased tooth contact). In some embodiments, the force modeling does not include attractive forces between opposite jaws or between teeth in opposite jaws.

The force modeling and adjustment module 1197 can be configured to identify one of the number of repulsive forces having a magnitude that is different than others of the number of repulsive forces by a statistically significant amount. The repulsive forces can be generated according to collisions between teeth in opposite jaws that arise from the first jaw being moved toward the second jaw. The one of the number of repulsive forces having the statistically significant different magnitude can indicate one or more corresponding teeth that are preventing good occlusion for the virtual dental model 1151.

The force modeling and adjustment module 1197 can be configured to determine a positional adjustment to one of the number of points corresponding to the statistically significantly different repulsive force to reduce the difference. The force modeling and adjustment module 1197 can be configured to assign a first allocation of the positional adjustment to the tooth including the one of the number of points and to assign a second allocation of the positional adjustment to one of the first jaw and the second jaw including the tooth. Thus, the tooth presumed to be preventing good occlusion can be "corrected" first.

The force modeling and adjustment module 1197 can be configured to limit the second allocation based on a range of motion of the one of the first jaw and the second jaw. The force modeling and adjustment module 1197 can be configured to maximize the second allocation within the limit of the range of motion.

The treatment module 1199 can be configured to define a number of treatment steps between a first arrangement of teeth in the first jaw and the second jaw and a second arrangement of teeth in the first jaw and the second jaw based on the positional adjustment.

The system 1180 can be further configured to iteratively move the first jaw toward the second jaw, model the number of repulsive forces, identify one of the number of repulsive forces, determine a positional adjustment, and assign a first and a second allocation of the positional adjustment. Thus, as the system 1180 progresses after correcting one tooth that may be preventing good occlusion, it can make an adjustment, and identity and correct another tooth that may be preventing good occlusion.

The system 1180 can be further configured to iterate until none of the number of repulsive forces have a magnitude that is different than others of the number of repulsive forces by a statistically significant amount. That is, the system 1180 can automatically achieve a desirable final position for the teeth in the virtual dental model 1151.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the use of the terms "a", "an", "one or more", "a number of", or "at least one" are all to be interpreted as meaning one or more of an item is present. Additionally, it is to be understood that the above description has been made in an illustrative fashion, and not a restrictive one. Combination of the above embodiments, and other embodiments not specifically described herein will be apparent to those of skill in the art upon reviewing the above description.

It will be understood that when an element is referred to as being "on," "connected to" or "coupled with" another element, it can be directly on, connected, or coupled with the other element or intervening elements may be present. In contrast, when an element is referred to as being "directly on," "directly connected to" or "directly coupled with" another element, there are no intervening elements or layers present. As used herein, the term "and/or" includes any and all combinations of one or more of the associated listed items.

It will be understood that, although the terms first, second, etc. may be used herein to describe various elements and that these elements should not be limited by these terms. These terms are only used to distinguish one element from another element. Thus, a first element could be termed a second element without departing from the teachings of the present disclosure.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in a single embodiment for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A method of using a virtual dental model to design a series of orthodontic appliances, the method comprising:
   determining closest mesh vertex pairs of the virtual dental model by bounding the virtual dental model with a first box, dividing the first box into a plurality of coarse boxes, subdividing a subset of the plurality of coarse boxes that are near a mesh vertex into a plurality of fine boxes, and determining the closest mesh vertex pairs for the plurality of coarse boxes and the plurality of fine boxes;
   optimizing an energy function by simulating biting using the closest mesh vertex pairs of the virtual dental model the virtual dental model including an upper jaw and a lower jaw in a preliminary target position, wherein optimizing the energy function includes adjusting a position of one or more teeth in the virtual dental model to accomplish one or more of:
      resolving a collision between corresponding teeth of the upper and lower jaws,
      closing a posterior space between corresponding teeth of the upper and lower jaws, and
      achieving a particular ridge-groove relationship between teeth of the upper and lower jaws; and
   defining a number of treatment steps between the preliminary target position and a final target position for the upper and lower jaws based on the optimized energy function, wherein each of the number of treatment steps corresponds to an amount of adjustment to be performed by a respective orthodontic appliance.

2. The method of claim 1, wherein optimizing the energy function includes successively simulating biting for a tooth of the upper jaw and a tooth of the lower jaw until the energy function is optimized for the tooth of the upper jaw and the tooth of the lower jaw within a desired accuracy.

3. The method of claim 1, wherein optimizing the energy function includes optimizing the energy function of all of the teeth of the virtual dental model during a biting simulation.

4. The method of claim 1, wherein optimizing the energy function includes creating a stable solution for the virtual dental model.

5. The method of claim 1, wherein achieving the particular ridge-groove relationship between teeth of the upper and lower jaws includes adjusting the position of the one or more teeth such that a ridge of a tooth of one of the upper or lower jaw fits into a groove of the corresponding upper or lower jaw.

6. The method of claim 1, wherein adjusting the position of one or more teeth includes adjusting the position of a number of posterior teeth of the upper jaw and a number of posterior teeth of the lower jaw in six degrees of freedom.

7. The method of claim 1, further comprising adjusting the position of one or more teeth after the energy function is optimized to achieve the final target position for the upper and lower jaws.

8. The method of claim 1, wherein optimizing the energy function includes assigning a weight to one or more variables in the energy function.

9. The method of claim 8, wherein assigning the weight to the one or more variables to assure movement of the one or more teeth is within a specified tolerance.

10. The method of claim 8, wherein assigning the weight includes more heavily weighting alignment for occlusion of anterior teeth and more heavily weighting contact and collision for posterior teeth compared to other variables.

11. The method of claim 1, wherein the preliminary target position is automatically defined or manually defined by a user.

12. The method of claim 1, further comprising creating the respective orthodontic appliance.

13. The method of claim 1, wherein resolving the collision between corresponding teeth of the upper and lower jaws comprises determining distances between the closest mesh vertex pairs of the upper and lower jaws.

14. The method of claim 1, wherein closing the posterior space between corresponding teeth of the upper and lower jaws comprises:
   determining that there is space between a mesh vertex of a first tooth of the lower jaw and a second tooth of the upper jaw, and
   creating a space force to pull the first tooth and the second tooth closer together.

15. A computing device readable physical medium having instructions which can be executed by a processor to cause a computing device to:
   determine closest mesh vertex pairs of a virtual dental model by bounding the virtual dental model with a first box, dividing the first box into a plurality of coarse boxes, subdividing a subset of the plurality of coarse boxes that are near a mesh vertex into a plurality of fine boxes, and determining the closest mesh vertex pairs for the plurality of coarse boxes and the plurality of fine boxes;

optimize an energy function by simulating biting using the closest mesh vertex pairs of the virtual dental model, the virtual dental model including an upper jaw and a lower jaw in a preliminary target position, wherein optimizing the energy function includes adjusting a position of one or more teeth in the virtual dental model to accomplish one or more of:
  resolving a collision between corresponding teeth of the upper and lower jaws,
  closing a posterior space between corresponding teeth of the upper and lower jaws, and
  achieving a particular ridge-groove relationship between teeth of the upper and lower jaws; and define a number of treatment steps between the preliminary target position and a final target position for the upper and lower jaws based on the optimized energy function, wherein each of the number of treatment steps corresponds to an amount of adjustment to be performed by a respective orthodontic appliance.

16. The medium of claim 15, wherein the instructions to optimize the energy function include instructions to successively simulate biting for a tooth of the upper jaw and a tooth of the lower jaw until the energy function is optimized for the tooth of the upper jaw and the tooth of the lower jaw within a desired accuracy.

17. The medium of claim 15, wherein the instructions to adjust the position of one or more teeth include instructions to adjust the position of a number of posterior teeth of the upper jaw and a number of posterior teeth of the lower jaw in six degrees of freedom.

18. The medium of claim 15, wherein the instructions to optimize the energy function include instructions to assign a weight to one or more variables in the energy function.

19. The medium of claim 18, wherein the instructions to assign the weight to the one or more variables assure movement of the one or more teeth is within a specified tolerance.

20. The medium of claim 18, wherein the instructions to assign the weight to the one or more variables include instructions to more heavily weight alignment for occlusion of anterior teeth and more heavily weight contact and collision for posterior teeth compared to other variables.

21. The medium of claim 18, wherein the instructions to optimize the energy function include instructions to iteratively adjust the position of one or more teeth and optimize the energy function, wherein the instructions to assign the weight to the one or more variables include instructions to:
  set a weight of collision as a first value for each iteration before a first number of iterations has been performed;
  increase the weight of collision by a second value for each iteration after the first number of iterations has been performed and before a second number of iterations has been performed, and
  increase the weight of collision by a third value for each iteration after the second number of iterations has been performed.

* * * * *